(12) United States Patent
Dabel

(10) Patent No.: US 11,497,892 B2
(45) Date of Patent: Nov. 15, 2022

(54) CLOSED CIRCUIT DRESSING SYSTEM FOR PICC SITES AND PICC LINES

(71) Applicant: Pascal Dabel, Los Angeles, CA (US)

(72) Inventor: Pascal Dabel, Los Angeles, CA (US)

( * ) Notice: Subject to any disclaimer, the term of this patent is extended or adjusted under 35 U.S.C. 154(b) by 85 days.

(21) Appl. No.: 16/947,280

(22) Filed: Jul. 27, 2020

(65) Prior Publication Data

US 2022/0023596 A1 Jan. 27, 2022

(51) Int. Cl.
*A61M 25/02* (2006.01)
*A61F 13/42* (2006.01)
*A61F 13/00* (2006.01)

(52) U.S. Cl.
CPC ............. *A61M 25/02* (2013.01); *A61F 13/42* (2013.01); *A61F 2013/00412* (2013.01); *A61M 2025/0266* (2013.01)

(58) Field of Classification Search
CPC ............ A61F 13/42; A61F 2013/00412; A61F 2013/00978; A61M 2025/0266; A61M 25/02; A61M 2025/0246; A61M 39/165; A61M 2025/026; A61B 2046/234; B32B 2535/00
See application file for complete search history.

(56) References Cited

U.S. PATENT DOCUMENTS

| | | | |
|---|---|---|---|
| 2,810,944 A * | 10/1957 | Sander | A44B 19/16 24/400 |
| 3,675,654 A | 7/1972 | Baker | |
| 3,731,685 A | 5/1973 | Eidus | |
| 7,749,531 B2 | 7/2010 | Booher | |
| 8,061,292 B2 | 11/2011 | Ahmed et al. | |
| 9,535,043 B2 | 1/2017 | Manion et al. | |
| 10,123,723 B2 | 11/2018 | Bobo, Sr. et al. | |
| 10,207,098 B2 | 2/2019 | Tennican | |
| 10,213,344 B2 | 2/2019 | Bogue et al. | |
| 10,543,343 B2 | 1/2020 | Woehr et al. | |
| 2006/0015079 A1 * | 1/2006 | Mandzij | A61F 5/4407 604/317 |
| 2007/0088281 A1 * | 4/2007 | Ritchey | A61F 15/004 604/174 |
| 2009/0198182 A1 | 8/2009 | Fujishima et al. | |
| 2014/0228807 A1 | 8/2014 | Hart | |
| 2015/0257833 A1 * | 9/2015 | Dabel | A61B 46/10 604/171 |
| 2015/0351970 A1 | 12/2015 | Dagger et al. | |
| 2016/0262672 A1 | 9/2016 | Hammond et al. | |
| 2016/0287741 A1 | 10/2016 | Harris et al. | |
| 2016/0362229 A1 * | 12/2016 | Hoskins | B65D 5/48026 |
| 2018/0296149 A1 | 10/2018 | Goral et al. | |
| 2018/0358124 A1 | 12/2018 | Scheuer et al. | |

(Continued)

FOREIGN PATENT DOCUMENTS

WO WO-2015166157 A1 * 11/2015 ............ A61M 25/02

*Primary Examiner* — Bhisma Mehta
*Assistant Examiner* — Phoebe Anne Staton
(74) *Attorney, Agent, or Firm* — Dunlap Bennett & Ludwig, PLLC

(57) ABSTRACT

A closed-circuit dressing system for preventing moisture contacting PICC sites is provided. The closed-circuit dressing system include a breathable bag for harboring the PICC line(s) and a dressing film that envelopes the PICC site, wherein a moisture indicator ring provided by the dressing film indicates moisture penetrating a dressing reinforcement along the periphery of the dressing film.

9 Claims, 3 Drawing Sheets

(56) References Cited

U.S. PATENT DOCUMENTS

2019/0046772 A1    2/2019  Jutras
2019/0099586 A1*   4/2019  Stankiewicz ........... B32B 27/10
2019/0239945 A1    8/2019  Ravuna et al.

* cited by examiner

CLOSED CIRCUIT DRESSING SYSTEM FOR PICC SITES AND PICC LINES

BACKGROUND OF THE INVENTION

The present invention relates to medical devices and, more particularly, a closed-circuit dressing for a peripherally inserted central catheter (PICC).

A PICC (or PICC line) is a form of intravenous access that can be used for a prolonged period of time (e.g., for long chemotherapy regimens).

Patients that have to use a PICC are not allowed to shower or swim for weeks and up to months at a time. The patients thereby become dirty, uncomfortable, and so their PICC site is more prone to infection. The only way a patient may clean themselves is by using a washcloth or sponge which promotes cross contamination of the catheter site. Further, the patients are at increased risk for blood stream infections since there are no appropriate methods of protecting the PICC site.

Currently, dressings for PICC lines consist of a securement device and film dressing. The film dressing may include gauze; however, gauze only protects the entry site into the skin and are not water resistant. Moreover, the gauze does not prevent contaminants from contacting the PICC or entry site into the skin. The securement device may be tape, but tape, like gauze, absorbs moisture, dead skin cells, and bacteria—all promote infection instead of preventing it. Further, the gauze and tape fall off easily, leaving little to no protection. In short, none of the current approaches have a water/moisture indicating rings or dressing to protect the ports.

As can be seen, there is a need for a closed-circuit dressing for a PICC site from the elements and thereby increases hygiene. The closed-circuit dressing of the present invention provides a breathable bag with a water-resistant cap allowing easy access to the PICC line ports, wherein the water-resistant cap includes a water/moisture indicator ring.

SUMMARY OF THE INVENTION

In one aspect of the present invention, a closed-circuit dressing system for a PICC site includes the following: a breathable bag extending from a distal end to a proximal end; the proximal end having an opening and a securement point; a dressing film having adhesive along one transparent surface, wherein a film periphery of the dressing film is dimensioned to circumscribe said PICC site; a moisture indicator ring inward of said film periphery; and a breathable film dressing reinforcement having an inner periphery generally coextensive with a ring periphery of the moisture indicator ring, and the breathable film dressing reinforcement having an outer periphery generally coextensive with said film periphery, whereby the securement point is overlain by the dressing film during use. In certain embodiments, the closed-circuit dressing system for a PICC site further includes either a slide connected to the distal end in such a way to move the distal end between an open condition and a closed condition or a pivot point connected to the distal end in such a way to move the distal end between a sealed condition and an accessible condition.

In another aspect of the present invention, a method of maintaining a moisture level of a PICC site of a patient includes the following: providing one of the above-mentioned closed-circuit dressing systems; placing one or more PICC lines through the opening of the proximal end of the breathable bag; securing the securement point to the patient; securing the dressing film over the PICC site and over the opening; and moving the distal end to the open condition or the accessible condition to engage the one or more PICC lines.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a closed-circuit dressing system for preventing moisture from contacting PICC sites. The closed-circuit dressing system has a breathable bag for harboring the PICC line(s) and a dressing film that envelopes the PICC site, wherein a moisture indicator ring provided by the dressing film indicates moisture penetrating a dressing reinforcement along the periphery of the dressing film.

Referring now to FIGS. 1 through 8, the present invention may include a closed-circuit dressing system 100 providing a breathable bag 10 and a dressing film 22 with moisture indicator ring 24.

Figure 8:
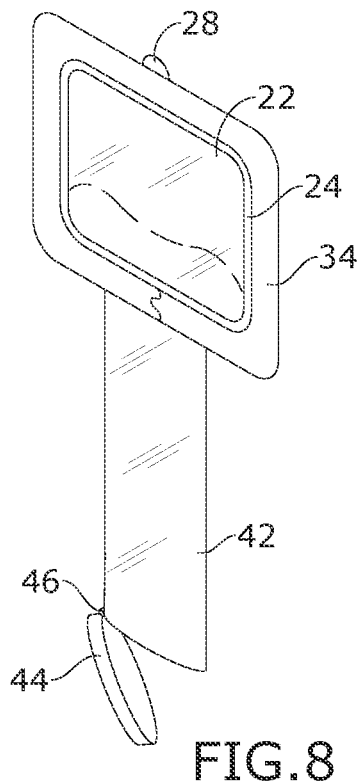
FIG. 8 is a perspective view of an exemplary embodiment of the present invention, illustrating a cap-like distal 44 in an accessible condition.

The breathable bag 10 extends from a proximal end 11 to a distal end 12. The distal end 12 may include a catheter access resealable seam with a slide 14 that allows the distal end 12 to move between an open condition and a closed condition. In certain embodiments, the breathable bag 10 provides a pivot point 46 for the distal end 44 in such a way that the distal end 44 is movable between a sealed condition and an accessible condition, as illustrated in FIG. 8. The breathable bag 10 may be made from a breathable polymer, polyurethane, or the like.

A securement 16 may be attached to the proximal end, the securement 16 may have a securement adhesive 18 along one surface for attaching the proximal end/securement 16 to a user. In certain embodiments, the securement adhesive 18 may have backing paper 20 for covering the securement adhesive 18 prior to employment.

The dressing film 22 may be transparent. The dressing film 22 may have a film periphery 21 dimensioned to circumscribe a PICC site. The dressing film 22 may have dressing adhesive 30 along one surface for attaching the dressing film 22 to a user. In certain embodiments, the dressing adhesive 30 may have dressing backing paper 32 for covering the dressing adhesive 30 prior to employment.

Figure 6:
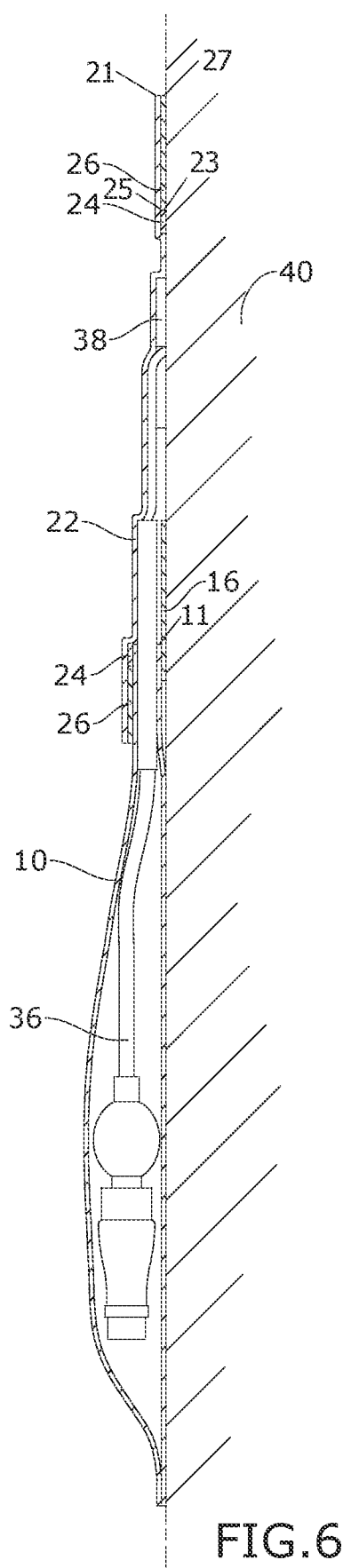
FIG. 6 is a section view view of an exemplary embodiment of the present invention, taken along line 6-6 in FIG. 1, with PICC line(s) 36 and biopatch 38 in full for clarity.
Figure 7:
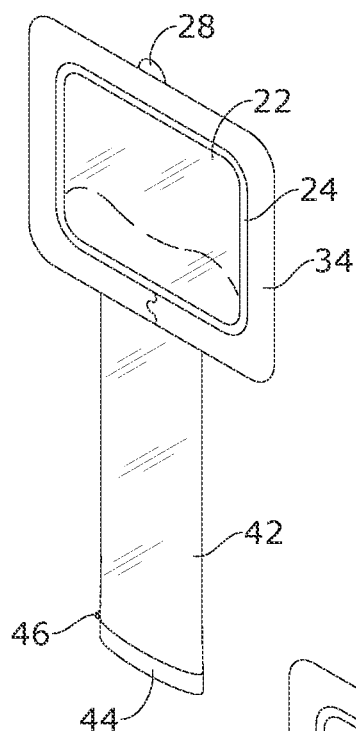
FIG. 7 is a perspective view of an exemplary embodiment of the present invention, illustrating bag closure.

A breathable film dressing reinforcement 26 with a fabric mesh may be dimensioned to have an outer periphery 27 equal or less than a dressing periphery of the dressing film 22. The moisture indicator ring 24 may be dimensioned to have an outer periphery 23 equal or less than an inner periphery 25 of the breathable film dressing reinforcement 26, as illustrated in FIG. 6. Thus, in an assembled condition, the breathable film dressing reinforcement 26 and the moisture indicator ring 24 are coplanar with the moisture indicator ring 24 inside the breathable film dressing reinforcement 26, and the dressing film 22 overlaying both so that the dressing adhesive 30 adheres to both, as well as the skin of the patient around the PICC site.

The breathable film dressing reinforcement 26 may have a removable tab 28 extending from a portion of its outer periphery. A fabric protective paper 34 may engage the breathable film dressing reinforcement 26 prior to employment.

Figure 1:
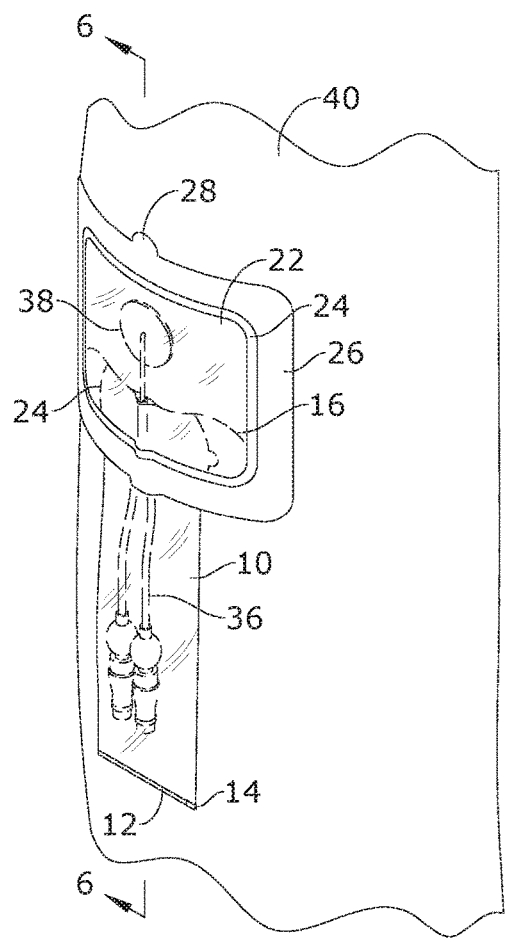
FIG. 1 is a perspective view of an exemplary embodiment of the present invention, shown in use.
Figure 2:
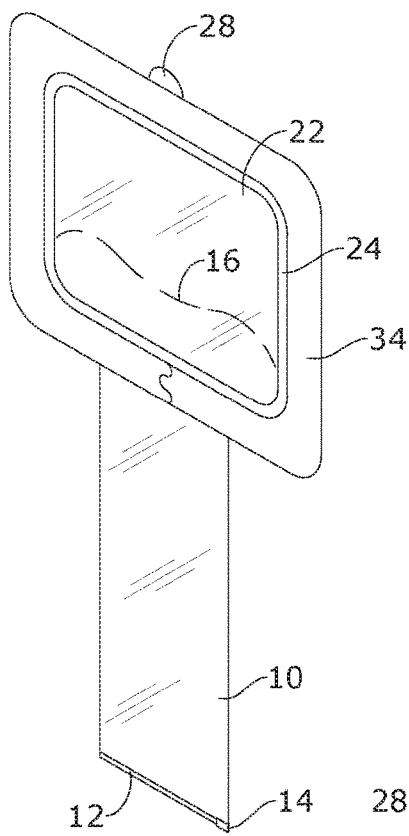
FIG. 2 is a front perspective view of an exemplary embodiment of the present invention before application.
Figure 3:
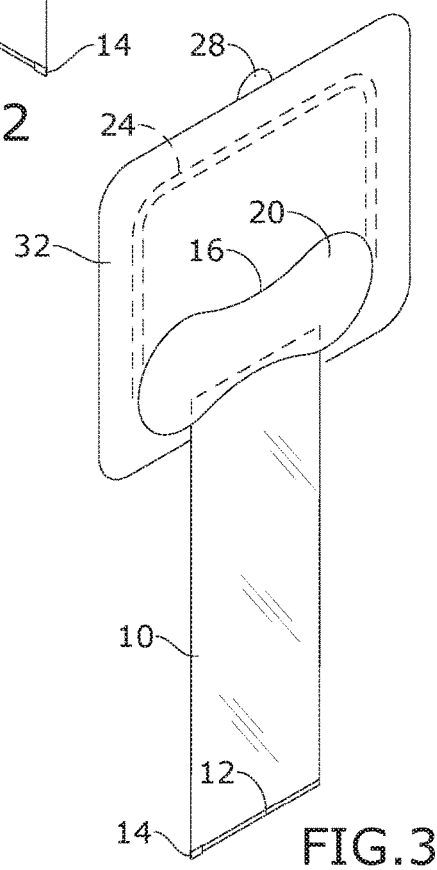
FIG. 3 is a rear perspective view of an exemplary embodiment of the present invention before application.
Figure 4:
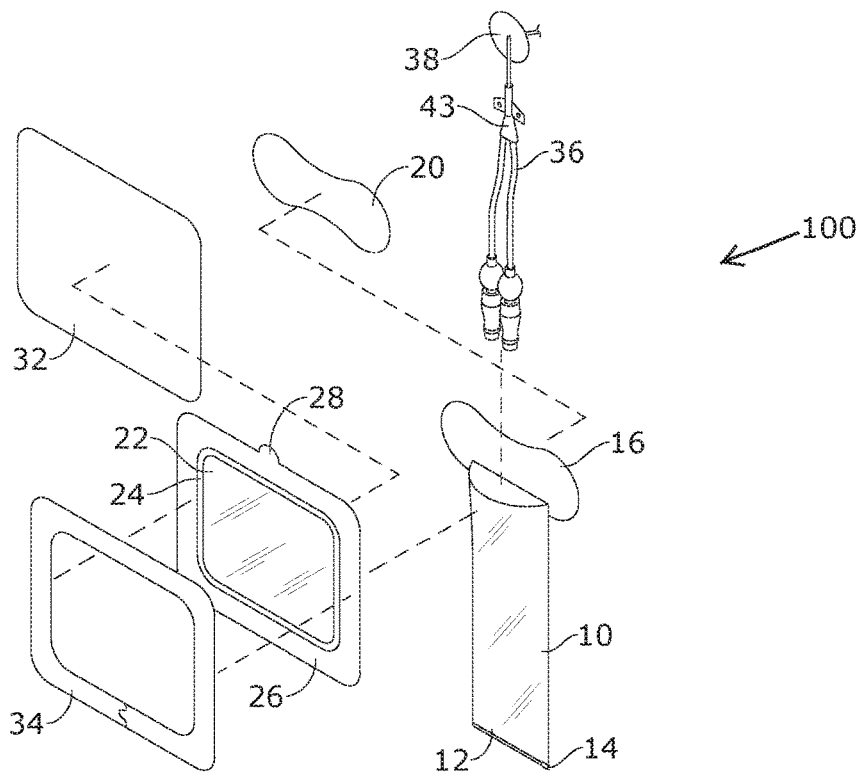
FIG. 4 is a front exploded perspective view of an exemplary embodiment of the present invention, illustrating placement of PICC line(s) 36 into the breathable sleeve/bag 10.
Figure 5:
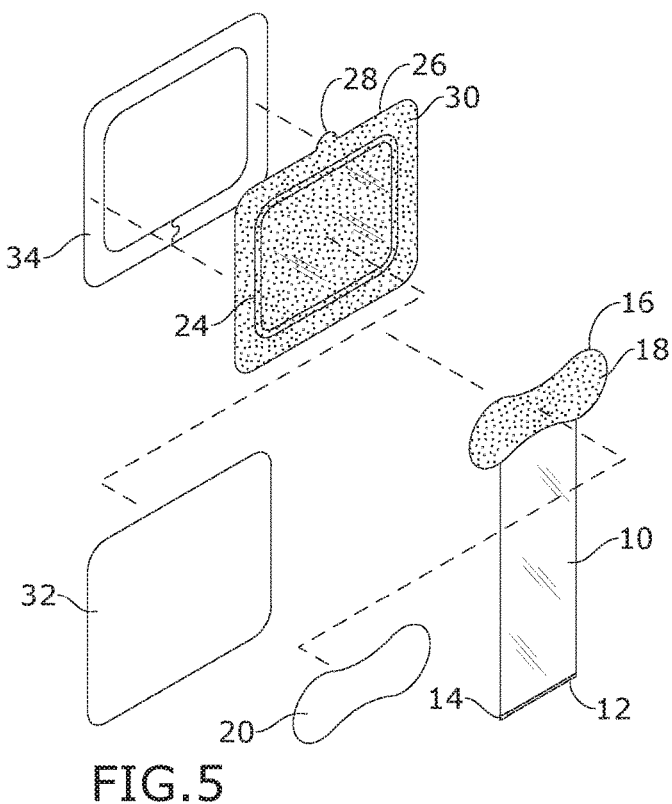
FIG. 5 is a rear exploded perspective view of an exemplary embodiment of the present invention.

A method of using the present invention may include the following. The closed-circuit dressing system 100 disclosed above may be provided. First a user may groom an area of the body around the PICC site, which may include shaving and/or cleaning the area. A biopatch 38 may cover the entry point of the PICC 43 at the PICC site. PICC line(s) 36 depend form the PICC 43, as illustrated in FIG. 4.

Then the dependent PICC line(s) 36 may be placed in the breathable bag 10 through the opening of the proximal end. The air may be squeezed out of the sleeve of the breathable bag 10. The securement 16 is attached to the patient 40 just downward of the PICC site/biopatch 38. The dressing film 22 may be lain over the PICC site/biopatch 38 so that the breathable film dressing reinforcement 26 circumscribes the PICC site/biopatch 38. The dressing film 22 may be adhered to the patient's skin by the dressing adhesive 30 pressed firmly against dry and hairless skin around the PICC site. This may prevent water from getting into the closed-circuit dressing system 100 or making contact with the PICC 43 in the shower or pool. If water were to accidentally get through the breathable film dressing reinforcement, the water may come into contact with the water indicator ring 24 which may cause a color change, for example from white to red, blue to white, or the like. The patient may then know to get out of the shower or pool and dry themselves off thoroughly. The device may then be removed from the skin by pulling on the tab 28 and discarded.

The breathable bag 10 has a high moisture/water vapor transmission rate which will prevent accumulation of moisture (sweat and condensation) inside of the closed-circuit environment once applied to the skin. Water cannot get into the closed-circuit dressing system 100 but moisture freely passes out at a rate higher than that of sweat produced from the area of skin being protected.

It should be understood, of course, that the foregoing relates to exemplary embodiments of the invention and that modifications may be made without departing from the spirit and scope of the invention as set forth in the following claims.

What is claimed is:

1. A closed-circuit dressing system for a peripherally inserted central catheter (PICC) site, comprising:
   a breathable bag extending from a distal end to a proximal end;
   the proximal end having an opening;
   a dressing film having adhesive along an entirety of one transparent surface, wherein a film periphery of the dressing film is dimensioned to circumscribe said PICC site;
   a moisture indicator ring inward of said film periphery; and
   a breathable film dressing reinforcement having an inner periphery generally coextensive with a ring periphery of the moisture indicator ring, and the breathable film dressing reinforcement having an outer periphery generally coextensive with said film periphery, wherein the moisture indicator ring and the breathable film dressing reinforcement are disposed along the one transparent surface in such a way as to be coplanar and contiguous along their respective ring and inner peripheries,
   whereby the opening is overlain by and visible through the dressing film during use.

2. The closed-circuit dressing system for a PICC site of claim 1, further comprising:
   a slide operatively associated with a resealable seam of the distal end in such a way to move the distal end between an open condition and a closed condition.

3. A method of maintaining a moisture level of a PICC site of a patient, the method comprising:
   providing the closed-circuit dressing system for a PICC site of claim 2;
   placing one or more PICC lines through the opening of the proximal end of the breathable bag;
   securing said proximal end to the patient;
   securing the dressing film over the PICC site and over the opening; and
   moving the distal end to the open condition to engage the one or more PICC lines.

4. The closed-circuit dressing system for a PICC site of claim 1, further comprising:
   a pivot point connecting a cap to the distal end in such a way to move the distal end between a sealed condition and an accessible condition.

5. A method of maintaining a moisture level of a PICC site of a patient, the method comprising:
   providing the closed-circuit dressing system for a PICC site of claim 4;
   placing one or more PICC lines through the opening of the proximal end of the breathable bag;
   securing said proximal end to the patient;
   securing the dressing film over the PICC site and over the opening; and
   moving the distal end to the accessible condition to engage the one or more PICC lines.

6. A method of maintaining a moisture level of a PICC site of a patient, the method comprising:
   providing the closed-circuit dressing system for a PICC site of claim 1;
   placing one or more PICC lines through the opening of the proximal end of the breathable bag;
   securing said proximal end to the patient; and
   securing the dressing film over the PICC site and over said proximal end.

7. The closed-circuit dressing system for a PICC site of claim 1, where in use, the moisture indicator ring and the breathable film dressing reinforcement protrude away from the one transparent surface and toward a user.

8. The closed-circuit dressing system for a PICC site of claim 1, wherein the breathable film dressing reinforcement further includes a fabric mesh.

9. The closed-circuit dressing system for a PICC site of claim 1, further comprising a securement element attached to and extending substantially beyond the proximal end.

\* \* \* \* \*